(12) United States Patent
Munrow et al.

(10) Patent No.: US 11,096,761 B2
(45) Date of Patent: Aug. 24, 2021

(54) METHODS AND SYSTEMS FOR CONTROLLED DEPLOYMENT OF NEEDLES IN TISSUE

(71) Applicant: Gynesonics, Inc., Redwood City, CA (US)

(72) Inventors: Michael Munrow, Belmont, CA (US); Jordan Bajor, Palo Alto, CA (US); Malcolm G. Munro, Tarzana, CA (US)

(73) Assignee: Gynesonics, Inc., Redwood City, CA (US)

( * ) Notice: Subject to any disclaimer, the term of this patent is extended or adjusted under 35 U.S.C. 154(b) by 0 days.

(21) Appl. No.: 17/028,596

(22) Filed: Sep. 22, 2020

(65) Prior Publication Data

US 2021/0000565 A1 Jan. 7, 2021

Related U.S. Application Data

(63) Continuation of application No. 15/595,659, filed on May 15, 2017, which is a continuation of application (Continued)

(51) Int. Cl.
*A61B 90/00* (2016.01)
*A61B 18/14* (2006.01)
(Continued)

(52) U.S. Cl.
CPC .......... *A61B 90/36* (2016.02); *A61B 10/0045* (2013.01); *A61B 18/1477* (2013.01);
(Continued)

(58) Field of Classification Search
None
See application file for complete search history.

(56) References Cited

U.S. PATENT DOCUMENTS

| 4,289,132 A | 9/1981 | Rieman |
| 4,671,292 A | 6/1987 | Matzuk |

(Continued)

FOREIGN PATENT DOCUMENTS

| JP | H07306714 A | 11/1995 |
| JP | H11508790 A | 8/1999 |

(Continued)

OTHER PUBLICATIONS

Alterovitz, et al. Simulating Needle Insertion and Radioactive Seed Implantation for Prostate Brachytherapy. Medicine Meets Virtual Reality 11, Westwood et al. (Eds.), IOS Press, Jan. 2003, pp. 19-25.

(Continued)

*Primary Examiner* — Katherine L Fernandez
(74) *Attorney, Agent, or Firm* — Wilson Sonsini Goodrich and Rosati, P.C.

(57) ABSTRACT

Needles are deployed in tissue under direct ultrasonic or other imaging. To aid in deploying the needle, a visual needle guide is projected on to the image prior to needle deployment. Once the needle guide is properly aligned, the needle can be deployed. After needle deployment, a safety boundary and treatment region are projected on to the screen. After confirming that the safety boundary and treatment regions are sufficient, the patient can be treated using the needle.

21 Claims, 14 Drawing Sheets

Related U.S. Application Data

No. 13/589,975, filed on Aug. 20, 2012, now abandoned, which is a continuation of application No. 13/307,304, filed on Nov. 30, 2011, now Pat. No. 8,262,577, which is a continuation of application No. 12/245,567, filed on Oct. 3, 2008, now Pat. No. 8,088,072.

(60) Provisional application No. 60/979,613, filed on Oct. 12, 2007.

(51) Int. Cl.
    *A61B 10/00*     (2006.01)
    *A61M 5/46*     (2006.01)
    *A61B 90/11*     (2016.01)
    *A61B 34/10*     (2016.01)
    *A61B 10/04*     (2006.01)

(52) U.S. Cl.
    CPC ............... *A61M 5/46* (2013.01); *A61B 90/11* (2016.02); *A61B 2010/045* (2013.01); *A61B 2018/1425* (2013.01); *A61B 2034/107* (2016.02); *A61B 2090/378* (2016.02)

(56) References Cited

U.S. PATENT DOCUMENTS

| | | | |
|---|---|---|---|
| 4,802,487 A | 2/1989 | Martin et al. | |
| 4,936,281 A | 6/1990 | Stasz | |
| 5,269,301 A | 12/1993 | Cohen | |
| 5,372,587 A | 12/1994 | Hammerslag et al. | |
| 5,456,689 A | 10/1995 | Kresch et al. | |
| 5,471,988 A | 12/1995 | Fujio et al. | |
| 5,492,126 A | 2/1996 | Hennige et al. | |
| 5,527,331 A | 6/1996 | Kresch et al. | |
| 5,531,676 A | 7/1996 | Edwards et al. | |
| 5,607,389 A | 3/1997 | Edwards et al. | |
| 5,649,911 A | 7/1997 | Trerotola | |
| 5,662,664 A | 9/1997 | Gordon et al. | |
| 5,666,954 A | 9/1997 | Chapelon et al. | |
| 5,697,897 A | 12/1997 | Buchholtz et al. | |
| 5,730,752 A | 3/1998 | Alden et al. | |
| 5,741,287 A | 4/1998 | Alden et al. | |
| 5,769,880 A | 6/1998 | Truckai et al. | |
| 5,860,974 A | 1/1999 | Abele et al. | |
| 5,863,294 A | 1/1999 | Alden | |
| 5,873,828 A | 2/1999 | Fujio et al. | |
| 5,876,340 A | 3/1999 | Tu et al. | |
| 5,876,399 A | 3/1999 | Chia et al. | |
| 5,891,137 A | 4/1999 | Chia et al. | |
| 5,906,615 A | 5/1999 | Thompson | |
| 5,908,385 A | 6/1999 | Chechelski et al. | |
| 5,916,198 A | 6/1999 | Dillow | |
| 5,931,787 A | 8/1999 | Dietz et al. | |
| 5,957,941 A | 9/1999 | Ream | |
| 5,964,740 A | 10/1999 | Ouchi | |
| 5,979,452 A | 11/1999 | Fogarty et al. | |
| 5,979,453 A | 11/1999 | Savage et al. | |
| 5,984,942 A | 11/1999 | Alden et al. | |
| 6,002,968 A | 12/1999 | Edwards | |
| 6,007,499 A | 12/1999 | Martin et al. | |
| 6,032,673 A | 3/2000 | Savage et al. | |
| 6,039,748 A | 3/2000 | Savage et al. | |
| 6,055,449 A | 4/2000 | Navab | |
| 6,059,766 A | 5/2000 | Greff | |
| 6,077,257 A | 6/2000 | Edwards et al. | |
| 6,141,577 A | 10/2000 | Rolland et al. | |
| 6,146,378 A | 11/2000 | Mikus et al. | |
| 6,146,380 A | 11/2000 | Racz et al. | |
| 6,149,598 A | 11/2000 | Tanaka | |
| 6,158,250 A | 12/2000 | Tibbals, Jr. et al. | |
| 6,171,249 B1 | 1/2001 | Chin et al. | |
| 6,190,383 B1 | 2/2001 | Schmaltz et al. | |
| 6,193,714 B1 | 2/2001 | McGaffigan et al. | |
| 6,211,153 B1 | 4/2001 | Garnick et al. | |
| 6,216,029 B1 | 4/2001 | Paltieli | |
| 6,238,336 B1 | 5/2001 | Ouchi | |
| 6,241,725 B1 | 6/2001 | Cosman | |
| 6,254,601 B1 | 7/2001 | Burbank et al. | |
| 6,280,441 B1 | 8/2001 | Ryan | |
| 6,296,639 B1 | 10/2001 | Truckai et al. | |
| 6,306,129 B1 | 10/2001 | Little et al. | |
| 6,311,084 B1 | 10/2001 | Cormack et al. | |
| 6,314,310 B1 | 11/2001 | Ben-Haim et al. | |
| 6,315,741 B1 | 11/2001 | Martin et al. | |
| 6,325,758 B1 | 12/2001 | Carol et al. | |
| 6,379,348 B1 | 4/2002 | Onik | |
| 6,405,732 B1 | 6/2002 | Edwards et al. | |
| 6,419,648 B1 | 7/2002 | Vitek et al. | |
| 6,419,653 B1 | 7/2002 | Edwards et al. | |
| 6,419,673 B1 | 7/2002 | Edwards et al. | |
| 6,425,867 B1 | 7/2002 | Vaezy et al. | |
| 6,432,067 B1 | 8/2002 | Martin et al. | |
| 6,447,477 B2 | 9/2002 | Burney et al. | |
| 6,461,296 B1 | 10/2002 | Desai | |
| 6,463,331 B1 | 10/2002 | Edwards | |
| 6,482,203 B2 | 11/2002 | Paddock et al. | |
| 6,485,413 B1 | 11/2002 | Boppart et al. | |
| 6,506,154 B1 | 1/2003 | Ezion et al. | |
| 6,506,156 B1 | 1/2003 | Jones et al. | |
| 6,506,171 B1 | 1/2003 | Vitek et al. | |
| 6,507,747 B1 | 1/2003 | Gowda et al. | |
| 6,508,815 B1 | 1/2003 | Strul et al. | |
| 6,522,142 B1 | 2/2003 | Freundlich | |
| 6,540,677 B1 | 4/2003 | Angelsen et al. | |
| 6,543,272 B1 | 4/2003 | Vitek | |
| 6,544,176 B2 | 4/2003 | Mikus et al. | |
| 6,550,482 B1 | 4/2003 | Burbank et al. | |
| 6,554,780 B1 | 4/2003 | Sampson et al. | |
| 6,559,644 B2 | 5/2003 | Froundlich et al. | |
| 6,569,159 B1 | 5/2003 | Edwards et al. | |
| 6,572,613 B1 | 6/2003 | Ellman et al. | |
| 6,575,969 B1* | 6/2003 | Rittman, III | A61B 18/1482 606/41 |
| 6,579,298 B1 | 6/2003 | Bruneau et al. | |
| 6,589,237 B2 | 7/2003 | Woloszko et al. | |
| 6,592,559 B1 | 7/2003 | Pakter et al. | |
| 6,602,251 B2 | 8/2003 | Burbank et al. | |
| 6,610,054 B1 | 8/2003 | Edwards et al. | |
| 6,612,988 B2 | 9/2003 | Maor et al. | |
| 6,613,004 B1 | 9/2003 | Vitek et al. | |
| 6,613,005 B1 | 9/2003 | Friedman et al. | |
| 6,623,481 B1 | 9/2003 | Garbagnati et al. | |
| 6,626,832 B1 | 9/2003 | Paltieli et al. | |
| 6,626,854 B2 | 9/2003 | Friedman et al. | |
| 6,626,855 B1 | 9/2003 | Weng et al. | |
| 6,632,193 B1 | 10/2003 | Davison et al. | |
| 6,635,055 B1 | 10/2003 | Cronin | |
| 6,635,065 B2 | 10/2003 | Burbank et al. | |
| 6,638,275 B1 | 10/2003 | McGaffigan et al. | |
| 6,638,286 B1 | 10/2003 | Burbank et al. | |
| 6,645,162 B2 | 11/2003 | Friedman et al. | |
| 6,652,516 B1 | 11/2003 | Gough | |
| 6,654,202 B2 | 11/2003 | Rea et al. | |
| 6,660,002 B1 | 12/2003 | Edwards et al. | |
| 6,660,024 B1 | 12/2003 | Flaherty et al. | |
| 6,663,624 B2 | 12/2003 | Edwards et al. | |
| 6,663,626 B2 | 12/2003 | Truckai et al. | |
| 6,666,833 B1 | 12/2003 | Friedman et al. | |
| 6,679,855 B2 | 1/2004 | Horn et al. | |
| 6,685,639 B1 | 2/2004 | Wang et al. | |
| 6,689,128 B2 | 2/2004 | Sliwa et al. | |
| 6,692,490 B1 | 2/2004 | Edwards | |
| 6,695,786 B2 | 2/2004 | Wang et al. | |
| 6,701,931 B2 | 3/2004 | Sliwa et al. | |
| 6,705,994 B2 | 3/2004 | Vortman et al. | |
| 6,712,815 B2 | 3/2004 | Sampson et al. | |
| 6,716,184 B2 | 4/2004 | Vaezy et al. | |
| 6,719,755 B2 | 4/2004 | Sliwa et al. | |
| 6,728,571 B1 | 4/2004 | Barbato | |
| 6,730,081 B1 | 5/2004 | Desai | |
| 6,733,458 B1 | 5/2004 | Steins et al. | |
| 6,735,461 B2 | 5/2004 | Vitek et al. | |

(56) References Cited

U.S. PATENT DOCUMENTS

| | | |
|---|---|---|
| 6,743,184 B2 | 6/2004 | Sampson et al. |
| 6,746,447 B2 | 6/2004 | Davison et al. |
| 6,764,488 B1 | 7/2004 | Burbank et al. |
| 6,773,431 B2 | 8/2004 | Eggers et al. |
| 6,786,870 B2 | 9/2004 | Miyaki et al. |
| 6,790,180 B2 | 9/2004 | Vitek |
| 6,805,128 B1 | 10/2004 | Pless et al. |
| 6,805,129 B1 | 10/2004 | Pless et al. |
| 6,813,520 B2 | 11/2004 | Truckai; Csaba et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 | 1/2005 | Lee |
| 6,921,398 B2 | 7/2005 | Carmel et al. |
| 6,936,048 B2 | 8/2005 | Hurst |
| 6,944,490 B1 | 9/2005 | Chow |
| 6,969,354 B1 | 11/2005 | Marian |
| 6,994,706 B2 | 2/2006 | Chornenky et al. |
| 7,160,296 B2 | 1/2007 | Pearson et al. |
| 7,171,255 B2 | 1/2007 | Holupka et al. |
| 7,229,401 B2 | 6/2007 | Kindlein |
| 7,247,141 B2 | 7/2007 | Makin et al. |
| 7,387,628 B1 | 6/2008 | Behl et al. |
| 7,517,346 B2 | 4/2009 | Sloan et al. |
| 7,963,941 B2 | 6/2011 | Wilk |
| 8,080,009 B2 | 12/2011 | Lee et al. |
| 8,088,072 B2 | 1/2012 | Munrow et al. |
| 8,157,741 B2 | 4/2012 | Hirota |
| 8,157,745 B2 | 4/2012 | Schoot |
| 8,216,231 B2 | 7/2012 | Behl et al. |
| 8,221,321 B2 | 7/2012 | McMorrow et al. |
| 8,262,577 B2 | 9/2012 | Munrow et al. |
| 8,287,485 B2 | 10/2012 | Kimura et al. |
| 8,377,041 B2 | 2/2013 | Frassica et al. |
| 8,469,893 B2 | 6/2013 | Chiang et al. |
| 8,512,330 B2 | 8/2013 | Epstein et al. |
| 8,512,333 B2 | 8/2013 | Epstein et al. |
| 8,540,634 B2 | 9/2013 | Bruce et al. |
| 8,585,598 B2 | 11/2013 | Razzaque et al. |
| 8,622,911 B2 | 1/2014 | Hossack et al. |
| 8,663,130 B2 | 3/2014 | Neubach et al. |
| 8,718,339 B2 | 5/2014 | Tonomura et al. |
| 8,814,796 B2 | 8/2014 | Martin et al. |
| 9,089,287 B2 | 7/2015 | Sliwa et al. |
| 9,198,707 B2 | 12/2015 | McKay et al. |
| 9,198,719 B2 | 12/2015 | Murdeshwar et al. |
| 9,247,925 B2 | 2/2016 | Havel et al. |
| 9,439,627 B2 | 9/2016 | Case et al. |
| 9,510,898 B2 | 12/2016 | Epstein et al. |
| 9,516,996 B2 | 12/2016 | Diolaiti et al. |
| 2001/0014805 A1 | 8/2001 | Burbank et al. |
| 2001/0035189 A1 | 11/2001 | Dobak et al. |
| 2001/0051802 A1 | 12/2001 | Woloszko et al. |
| 2002/0002393 A1 | 1/2002 | Mitchell |
| 2002/0022835 A1 | 2/2002 | Lee |
| 2002/0040220 A1 | 4/2002 | Zvuloni et al. |
| 2002/0052600 A1 | 5/2002 | Davison et al. |
| 2002/0068871 A1 | 6/2002 | Mendlein et al. |
| 2002/0077550 A1 | 6/2002 | Rabiner et al. |
| 2002/0183735 A1 | 12/2002 | Edwards et al. |
| 2003/0009164 A1 | 1/2003 | Woloszko et al. |
| 2003/0014046 A1 | 1/2003 | Edwards et al. |
| 2003/0028111 A1 | 2/2003 | Vaezy et al. |
| 2003/0032896 A1 | 2/2003 | Bosley et al. |
| 2003/0078502 A1 | 4/2003 | Miyaki et al. |
| 2003/0130575 A1 | 7/2003 | Desai |
| 2003/0130655 A1 | 7/2003 | Woloszko et al. |
| 2003/0195420 A1 | 10/2003 | Mendlein et al. |
| 2003/0195496 A1 | 10/2003 | Maguire et al. |
| 2003/0199472 A1 | 10/2003 | Al-Hendy et al. |
| 2003/0216725 A1 | 11/2003 | Woloszko et al. |
| 2003/0216759 A1 | 11/2003 | Burbank et al. |
| 2004/0002699 A1 | 1/2004 | Ryan et al. |
| 2004/0006336 A1 | 1/2004 | Swanson |
| 2004/0030268 A1 | 2/2004 | Weng et al. |
| 2004/0049121 A1 | 3/2004 | Yaron |
| 2004/0054366 A1 | 3/2004 | Davison et al. |
| 2004/0064134 A1 | 4/2004 | Xiao et al. |
| 2004/0120668 A1 | 6/2004 | Loeb |
| 2004/0143252 A1 | 7/2004 | Hurst |
| 2004/0147920 A1 | 7/2004 | Keidar et al. |
| 2004/0153057 A1 | 8/2004 | Davison |
| 2004/0175399 A1 | 9/2004 | Schiffman et al. |
| 2004/0176760 A1 | 9/2004 | Qiu |
| 2004/0193028 A1 | 9/2004 | Jones et al. |
| 2004/0215182 A1 | 10/2004 | Lee |
| 2004/0230190 A1 | 11/2004 | Dahla et al. |
| 2004/0231772 A1 | 11/2004 | Leonard et al. |
| 2004/0254572 A1 | 12/2004 | McIntyre et al. |
| 2005/0033108 A1 | 2/2005 | Sawyer |
| 2005/0038340 A1 | 2/2005 | Vaezy et al. |
| 2005/0085718 A1 | 4/2005 | Shahidi |
| 2005/0085730 A1 | 4/2005 | Flesch et al. |
| 2005/0107781 A1 | 5/2005 | Ostrovsky et al. |
| 2005/0124882 A1 | 6/2005 | Ladabaum et al. |
| 2005/0149013 A1 | 7/2005 | Lee |
| 2005/0159676 A1* | 7/2005 | Taylor ............... A61B 10/0275 600/567 |
| 2005/0177209 A1 | 8/2005 | Leung et al. |
| 2005/0197577 A1 | 9/2005 | Makin et al. |
| 2005/0203399 A1* | 9/2005 | Vaezy ................ A61N 7/02 600/439 |
| 2005/0215990 A1 | 9/2005 | Govari |
| 2005/0216039 A1 | 9/2005 | Lederman |
| 2005/0228288 A1 | 10/2005 | Hurst |
| 2005/0255039 A1 | 11/2005 | Desai |
| 2005/0256405 A1 | 11/2005 | Makin et al. |
| 2006/0010207 A1 | 1/2006 | Akerman et al. |
| 2006/0058671 A1 | 3/2006 | Vitek et al. |
| 2006/0058680 A1 | 3/2006 | Solomon |
| 2006/0089636 A1 | 4/2006 | Christopherson et al. |
| 2006/0178665 A1 | 8/2006 | Sloan et al. |
| 2006/0184049 A1 | 8/2006 | Tsujita |
| 2006/0189972 A1* | 8/2006 | Grossman ............ A61B 18/1477 606/32 |
| 2006/0241368 A1 | 10/2006 | Fichtinger et al. |
| 2007/0006215 A1 | 1/2007 | Epstein et al. |
| 2007/0016183 A1 | 1/2007 | Lee et al. |
| 2007/0083082 A1 | 4/2007 | Kiser et al. |
| 2007/0161897 A1 | 7/2007 | Sasaki et al. |
| 2007/0161905 A1 | 7/2007 | Munrow |
| 2007/0232913 A1 | 10/2007 | Lau et al. |
| 2007/0239062 A1* | 10/2007 | Chopra ............... A61B 5/4381 600/549 |
| 2007/0249936 A1 | 10/2007 | Deckman et al. |
| 2007/0249939 A1 | 10/2007 | Gerbi et al. |
| 2008/0015664 A1 | 1/2008 | Podhajsky |
| 2008/0033493 A1 | 2/2008 | Deckman et al. |
| 2008/0147056 A1 | 6/2008 | Van Der Weide et al. |
| 2008/0228081 A1 | 9/2008 | Becker et al. |
| 2009/0043295 A1 | 2/2009 | Arnal et al. |
| 2009/0118613 A1 | 5/2009 | Krugman et al. |
| 2010/0262133 A1 | 10/2010 | Hoey et al. |
| 2010/0305439 A1 | 12/2010 | Shai et al. |
| 2012/0035474 A1 | 2/2012 | Deckman et al. |
| 2012/0071794 A1 | 3/2012 | Karni |
| 2012/0078134 A1 | 3/2012 | Munrow et al. |
| 2012/0165813 A1 | 6/2012 | Lee et al. |
| 2012/0209115 A1 | 8/2012 | Tonomura |
| 2012/0271277 A1 | 10/2012 | Fischell et al. |
| 2012/0277737 A1 | 11/2012 | Curley |
| 2012/0316440 A1 | 12/2012 | Munrow et al. |
| 2013/0281863 A1 | 10/2013 | Chiang et al. |
| 2013/0317366 A1 | 11/2013 | Hirayama et al. |
| 2014/0180273 A1 | 6/2014 | Nair |
| 2014/0276081 A1 | 9/2014 | Tegels |
| 2015/0150497 A1 | 6/2015 | Goldchmit |
| 2015/0173592 A1 | 6/2015 | Leeflang et al. |
| 2015/0257779 A1 | 9/2015 | Sinelnikov et al. |
| 2016/0151041 A1 | 6/2016 | Lee et al. |
| 2016/0278740 A1 | 9/2016 | Negrila et al. |
| 2016/0310042 A1 | 10/2016 | Kesten et al. |
| 2017/0245838 A1 | 8/2017 | Munrow et al. |

(56) References Cited

U.S. PATENT DOCUMENTS

| 2017/0245891 | A1 | 8/2017 | Munrow et al. |
|---|---|---|---|
| 2020/0229892 | A1 | 7/2020 | Munrow et al. |
| 2021/0038341 | A1 | 2/2021 | Munrow et al. |

FOREIGN PATENT DOCUMENTS

| JP | 2001340350 A | 12/2001 |
|---|---|---|
| JP | 2005058584 A | 3/2005 |
| JP | 2005323669 A | 11/2005 |
| JP | 2006513831 A | 4/2006 |
| JP | 2006255405 A | 9/2006 |
| JP | 2007144180 A | 6/2007 |
| JP | 2007215672 A | 8/2007 |
| JP | 2007536063 A | 12/2007 |
| WO | WO-9811834 A1 | 3/1998 |
| WO | WO-9814169 A1 | 4/1998 |
| WO | WO-9927837 A2 | 6/1999 |
| WO | WO-9933394 A1 | 7/1999 |
| WO | WO-9943366 A1 | 9/1999 |
| WO | WO-0000098 A1 | 1/2000 |
| WO | WO-0113782 A1 | 3/2001 |
| WO | WO-0180723 A2 | 11/2001 |
| WO | WO-0195819 A1 | 12/2001 |
| WO | WO-0211639 A1 | 2/2002 |
| WO | WO-03005882 A2 | 1/2003 |
| WO | WO-03065908 A1 | 8/2003 |
| WO | WO-2004002293 A2 | 1/2004 |
| WO | WO-2004002550 A2 | 1/2004 |
| WO | WO-2004020011 A1 | 3/2004 |
| WO | WO-2004035110 A2 | 4/2004 |
| WO | WO-2004064658 A1 | 8/2004 |
| WO | WO-2005110255 A2 | 11/2005 |
| WO | WO-2006042117 A2 | 4/2006 |
| WO | WO-2006089426 A1 | 8/2006 |
| WO | WO-2009049082 A1 | 4/2009 |
| WO | WO-2014039795 A1 | 3/2014 |

OTHER PUBLICATIONS

Appeal Board Decision dated Mar. 2, 2018 for U.S. Appl. No. 13/589,975.
Bergamini, et al. Laparoscopic Radiofrequency Thermal Ablation: A New Approach to Symptomatic Uterine Myomas. Am. J. Obstetrics and Gynecology (2005) 192: 768-73.
Chopra et al. Radiofrequency ablation of hepatic tumors adjacent to the gallbladder: feasibility and safety. AJR Am J Roentgenol. Mar. 2003;180(3):697-701.
CNN.com Health Women. Experimental technique uses lasers to shrink uterine fibroids. Nov. 28, 2000.
"European Search Report dated Feb. 5, 2019 for EP18173696".
European Search Report and Search Opinion dated Apr. 5, 2016 for EP Application No. 08837389.9.
European search report dated Dec. 10, 2015 for EP Application No. 08837389.9.
Final Office action dated Jul. 16, 2019 for U.S. Appl. No. 15/597,511.
Hindley, et al. MRI guidance of focused ultrasound therapy of uterine fibroids: Early results. American Journal of Roentgenology, 2004, 183(6): 1173-1719.
International Search Report and Written Opinion dated Jan. 17, 2018 for International PCT Patent Application No. PCT/US2017/061366.
International search report and written opinion dated Feb. 12, 2009 for PCT/US2008/079400.
International Search Report and Written Opinion dated Apr. 6, 2017 for International PCT Patent Application No. PCT/US2017/014753.
Kanaoka, et al. Microwave endometrial ablation at a frequency of 2.45 Ghz. A pilot study. J Reprod Med. Jun. 2001; 46(60): 559-63.
Law, et al. Magnetic resonance-guided percutaneous laser ablation of uterine fibroids. J Magn Reson Imaging, Oct. 2000; 12(4):565-70.
Liu, et al. Catheter-Based Intraluminal Sonography. J. Ultrasound Med., 2004, 23:145-160.
Mogami, et al. Usefulness of MR-guided percutaneous cryotherapy. Med. Imaging Technol. 2004, 22(3): 131-6. (English abstract).
MSNBC OnLine Articles, About Us: Articles; "Intrauerine Fibroids Can Now Be Treated Nonsurgically" http://www.fibroids.com/news-blog/2004/08/intrauterine-fibroids-can-now-be-treated-nonsurgically/ Aug. 23, 2004.
Notice of allowance dated May 14, 2012 for U.S. Appl. No. 13/307,304.
Notice of allowance dated Oct. 25, 2011 for U.S. Appl. No. 12/245,567.
Office action dated Jan. 2, 2015 for U.S. Appl. No. 13/589,975.
"Office action dated Mar. 1, 2019 for U.S. Appl. No. 15/597,511.". 0.
Office Action dated Mar. 15, 2018 for U.S. Appl. No. 15/597,511.
Office action dated Mar. 18, 2020 for U.S. Appl. No. 15/595,659.
Office action dated Apr. 28, 2011 for U.S. Appl. No. 12/245,567.
Office action dated Apr. 29, 2020 for U.S. Appl. No. 16/841,201.
Office Action dated Jul. 31, 2017 for U.S. Appl. No. 15/597,511.
Office action dated Aug. 7, 2014 for U.S. Appl. No. 13/589,975.
Office action dated Aug. 10, 2015 for U.S. Appl. No. 13/589,975.
Office action dated Aug. 27, 2018 for U.S. Appl. No. 15/595,659.
Office action dated Sep. 19, 2019 for U.S. Appl. No. 15/595,659.
"Office action dated Oct. 10, 2017 for U.S. Appl. No. 15/595,659.".
Office action dated Nov. 21, 2013 for U.S. Appl. No. 13/589,975.
Office action dated Dec. 28, 2018 for U.S. Appl. No. 15/595,659.
Okamura, et al. Force Modeling for Needle Insertion into Soft Tissue. IEEE Transactions on Biomedical Engineering, Oct. 2001, 10 (51): 1707-1716.
RSNA 2000 Explore News Release. Lasers Liquify Uterine Fibroid Tumors. 11:30 a.m. CST, Monday, Nov. 27, 2000.
Senoh, et al. Saline Infusion Contrast Intrauterine Sonographic Assessment of the Endometrium with High-Frequency, Real-Time Miniature Transducer Normal Menstrual Cycle: a Preliminary Report. Human Reproduction, 14 (10): 2600-2603, 1999.
U.S. Appl. No. 60/938140, filed May 15, 2007.
Vascular and Interventional Radiology, SRSC; Nonsurgical Treatment of Uterine Fibroids. Available at http://www.drfibroid.com/treatment.htm. Accessed Apr. 11, 2011.
Websand, Inc., New treatment options for fibroid tumors, Copyright 2002 by WebSand, Inc.
EP20163750.1 Extended European Search Report dated Aug. 24, 2020.
Final Office action dated Nov. 3, 2020 for U.S. Appl. No. 16/841,201.
Office action dated Nov. 13, 2020 for U.S. Appl. No. 15/595,659.
Office action dated Dec. 10, 2020 for U.S. Appl. No. 17/028,593.

* cited by examiner

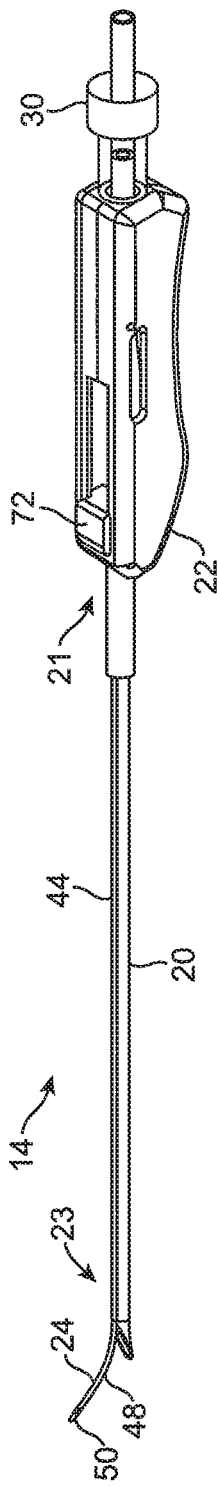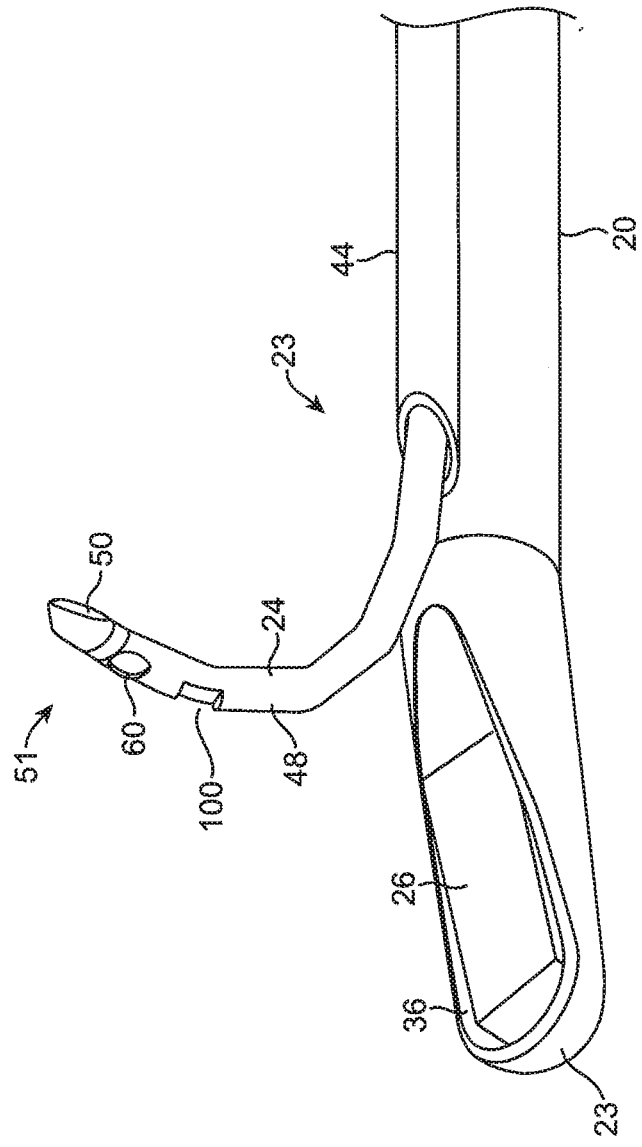
FIG. 2
FIG. 3

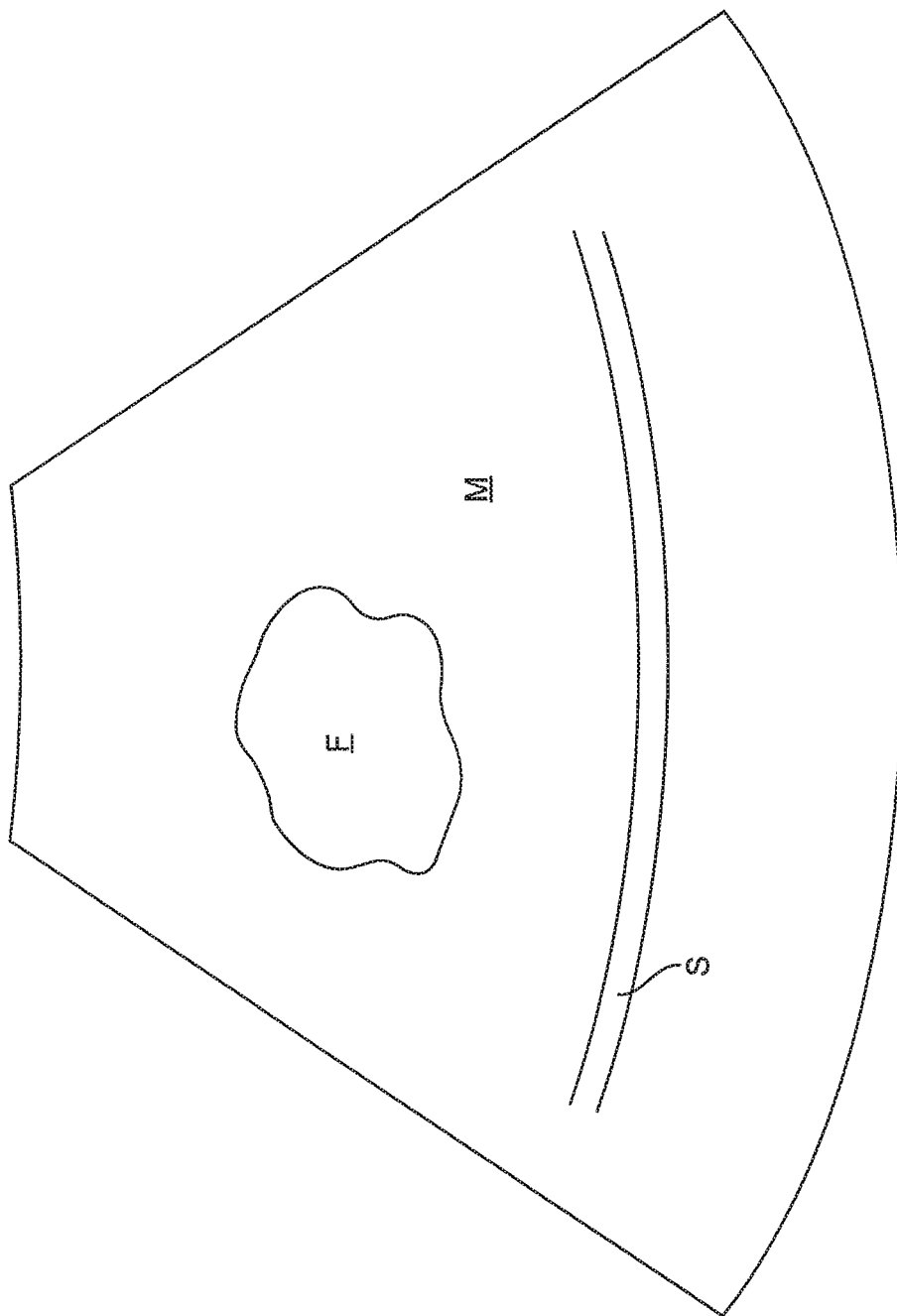

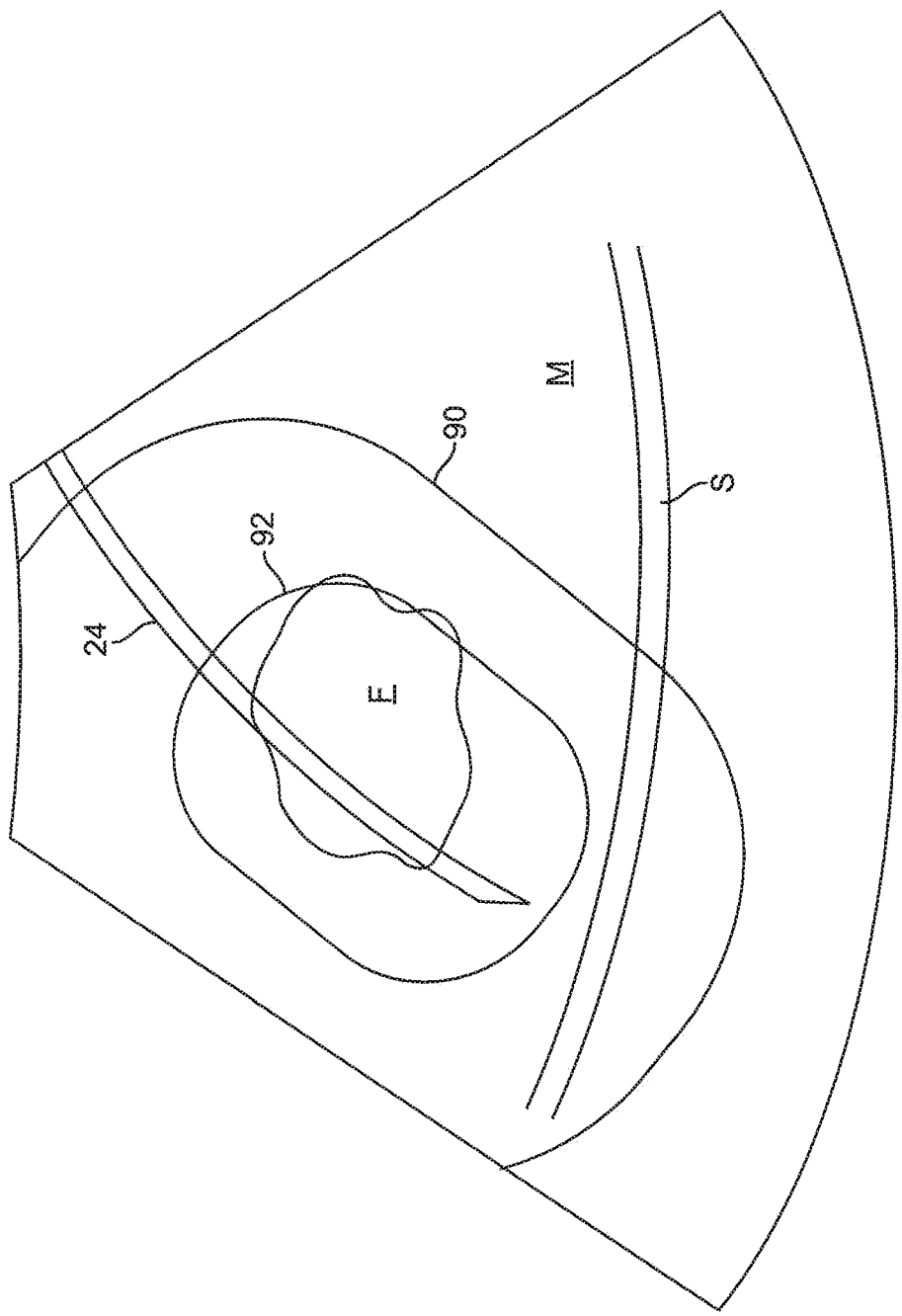

METHODS AND SYSTEMS FOR CONTROLLED DEPLOYMENT OF NEEDLES IN TISSUE

CROSS-REFERENCE TO RELATED APPLICATION

This application is a continuation of U.S. patent application Ser. No. 15/595,659, filed May 15, 2017; which is a continuation of U.S. patent application Ser. No. 13/589,975, filed Aug. 20, 2012; which is a continuation of U.S. patent application Ser. No. 13/307,304, filed Nov. 30, 2011, now U.S. Pat. No. 8,262,577; which is a continuation of U.S. patent application Ser. No. 12/245,567, filed on Oct. 3, 2008, now U.S. Pat. No. 8,088,072; which claims the benefit of Provisional Application No. 60/979,613, filed Oct. 12, 2007; the full disclosures of which are incorporated herein by reference.

BACKGROUND OF THE INVENTION

1. Field of the Invention

The present invention relates generally to medical methods and apparatus. More particularly, the present invention relates to methods and systems for controlling the deployment of needles using visual feedback from an ultrasonic or other image.

Current medical treatments of organs and tissues within a patient's body often use a needle or other elongate body for delivery of energy, therapeutic agents or the like. Optionally the methods use ultrasound imaging to observe and identify a treatment target and the position of the needle relative to the treatment target.

Of particular interest to the present invention, a treatment for uterine fibroids has recently been proposed which relies on the transvaginal positioning of a treatment device in the patient's uterus. A radiofrequency or other energy or therapeutic delivery needle is deployed from the device into the fibroid, and energy and/or therapeutic substances are delivered in order to ablate or treat the fibroid. To facilitate locating the fibroids and positioning the needles within the fibroids, the device includes an on-board ultrasonic imaging array with a field of view in a generally lateral direction from an axial shaft. A curved needle is advanced from the shaft and into the field of view so that the needle can be visualized and directed into the tissue and the targeted fibroid. The geometry of the needle deployment is advantageous since it permits the location and treatment of fibroids which are laterally adjacent to the shaft.

While effective and very beneficial for patients, such needle ablation and treatment protocols face several challenges. First, initial deployment of the needle can be difficult, particularly for physicians who have less experience. While the physician can view the tissue and target anatomy in real time on an imaging screen, it can be difficult to precisely predict the path the needle will take and assess its final treatment position. While the needle can certainly be partially or fully retracted and redeployed, it would be advantageous to minimize the number of deployments required before treatment is effected.

A second challenge comes after the needle has been deployed. While the position of the needle can be observed on the ultrasonic or other visual image, the treatment volume resulting from energy or other therapeutic delivery can be difficult to predict. As with initial positioning, experience will help but the need to exercise judgment and conjecture is best reduced.

A third challenge is in assuring that nearby sensitive tissue structures, such as the serosa surrounding the myometrium, are not unintentionally damaged. As with judging the treatment volume, predicting the safety margin of the treatment can be difficult.

For these reasons, it would be desirable to provide improved systems and methods for the deployment of energy delivery and other needles within ultrasonic or other imaging fields of view in energy delivery or other therapeutic protocols. It would be particularly useful to provide the treating physician with information which would assist in initial deployment of a needle in order to improve the likelihood that the needle will be properly positioned relative to a targeted anatomy to be treated. It would also be desirable, once the needle has been deployed, to provide feedback to the physician to assist in accurately predicting a treatment volume. Such information should allow the physician, if necessary, to reposition the needle in order to increase the likelihood of fully treating the anatomy. Furthermore, it would be desirable to provide feedback to the physician allowing the physician to assess a safety margin so that sensitive tissue structures are not damaged. All such feedback other information are preferably provided visually on the ultrasonic or other imaging screen so that the needle position can be quickly predicted, assessed, and treatment initiated. At least some of these objectives will be met by the inventions described hereinafter.

2. Description of the Background Art

U.S. Patent Publication No. 2006/0189972, published on Aug. 24, 2006 and commonly assigned with the present application, describes probes useful for both imaging and treating uterine fibroids, which probes could be used in the systems and methods of the present application. Other commonly assigned applications describing probes useful for treating uterine fibroids in the systems and methods of the present invention include application Ser. No. 11/409,496, filed on Apr. 20, 2006; Ser. No. 11/564,164, filed on Nov. 20, 2006; Ser. No. 11/620,594, filed on Jan. 5, 2007; and copending provisional application No. 60/938,140, filed on May 15, 2007, the full disclosures of which are incorporated herein by reference. Other related, commonly assigned applications are Ser. No. 11/620,569, filed Jan. 5, 2007; and Ser. No. 11/775,452, filed on Jul. 10, 2007. The full disclosures of each of these commonly owned, pending applications are incorporated herein by reference.

BRIEF SUMMARY OF THE INVENTION

The present invention provides both methods and systems for deploying one or more needles in tissue. The needles are usually intended to deliver a therapy to the tissue, most typically being adapted to deliver radiofrequency, plasma, heat, or other energy to ablate or otherwise modify the tissue or a targeted anatomy within the tissue. In other embodiments of the present invention, however, particularly those relating to initial needle deployment, the needles could also be intended for biopsy or have other diagnostic purposes.

One or more needles are deployed in tissue where the tissue is being imaged so that at least a portion of the needle (once deployed) and at least one anatomical feature within the tissue will be visible, preferably on a display screen in real time before, after, and/or during needle deployment. In a first specific aspect of the present invention, the image is overlaid with projected needle treatment information. By "projected," it is meant that the needle treatment information is predicted or calculated based on known or determined system information. For example, the shape of the needle and mechanics of the needle deployment system may be used to predict the path that the needle may take into tissue, as described in greater detail below. The treatment volume and safety boundaries or margins may be calculated or predicted based on the energy delivery characteristics of the system together with the anticipated tissue characteristics. The information overlaid on the image will allow a user, typically a treating physician, to evaluate the predicted and/or actual needle positions relative to both treatment efficacy and safety.

In the exemplary embodiments, at least one needle will be deployed from a probe where the probe may be introduced to the uterus or other body cavity or lumen. Exemplary anatomical features that may be imaged and subsequently treated or biopsied include fibroids, tumors, encapsulated tissue masses, pseudoencapsulated tissue masses, and the like. Of particular interest to the present invention, the probe may be positioned in the uterus and the needle deployed to a location proximate or into a fibroid located in the myometrium surrounding the uterus. In such cases, it will usually be desirable to also image the serosa which surrounds the myometrium and/or other sensitive anatomical features that could be damaged by the energy-mediated or other therapeutic treatment.

Thus, in a first specific aspect of the present invention, the projected needle information will include at least a projected safety boundary which provides a visual image of the treatment volume that can be provided through the needle. In such cases, evaluating can comprise confirming that the serosa or other sensitive tissue or anatomical structure is outside of the projected safety boundary (where tissue within the projected safety boundary is at risk of tissue damage). The projected safety boundary will usually provide a minimum distance between the needle and the serosa or other sensitive anatomical feature which is at least 0.5 cm, often being at least 0.7 cm, and preferably being at least 1 cm.

In a second specific aspect of the present invention, the projected needle treatment information will comprise a projected needle deployment path. The projected needle deployment path will typically find use prior to needle deployment where the treating physician can manipulate the probe which carries the needle so that the projected needle treatment path visible on the display screen is aligned so that the needle will enter or at least be reasonably close to the targeted anatomy to be treated. The projected needle treatment information will be based on the known mechanical characteristics of the needle and may vary for different needles. In some instances, it will be desirable to actually test individual needles which are being used so that their individual characteristics are known, but this will usually not be necessary. It will be appreciated that the actual needle entry path, while predictable within certain tolerances, may differ from the projected path due to differences in the tissue characteristics, small differences in the deployment mechanisms, differences in the needle characteristics, or other reasons. In such instances, the methods and systems of the present invention will allow for inputting the actual treatment position so that the safety and treatment boundaries can be predicted based on the actual needle position, not the predicted needle position. For example, the physician may locate a known point or artifact on the needle which appears in the visual image. By then "clicking on" that point or otherwise feeding that positional information back into the imaging and control system, the system can recalculate the actual needle position and, based on the actual position, calculate the safety and treatment boundaries.

In a third specific aspect of the present invention, the projected needle treatment information comprises a projected therapy region. The projected therapy region will be a boundary or volume which is shown on the visual display to allow the treating physician to assess whether the target region to be treated will likely be effectively treated based on the needle position. As just discussed, usually the projected needle treatment information is preferably based on the actual needle position but could also be based on the projected needle position. Thus, it may be possible for the treating physician to rely on a projected therapy region (as well as a projected safety boundary) while the projected needle position is being manipulated relative to the targeted anatomy to be treated. After actual deployment, the system can recalculate both the projected therapy region and the projected safety boundary to allow the treating physician to confirm both that the treatment will likely be effective and that the serosa and/or other sensitive tissue structures will not be damaged.

In a further specific aspect of the present invention, the treatment system will provide for an interlock or enablement step before treatment can be delivered to the tissue. For example, the system may require the treating physician to acknowledge that either or both of the safety boundary and treatment volumes have been observed and evaluated to determine that the treatment will be safe and/or effective. Without such acknowledgement, the system could preclude energy delivery until such time as the treating physician acknowledges evaluation of the safety and/or effectiveness. In other instances, the system could be modified to assess the projected boundaries relative to the targeted treatment anatomies and the sensitive tissue anatomy, although such fully automated systems are not presently preferred.

The methods of the present invention will preferably employ the uterine fibroid treatment probes, such as those described in the commonly owned, copending applications incorporated herein by reference above. These treatment probes comprise a shaft having both an imaging transducer and a deployable needle near the distal end. The needle is configured so that it may be selectively advanced in a generally lateral direction within the field of image of the transducer, typically an ultrasonic imaging array. After the needle has been advanced into the tissue, and the safety and effectiveness of the needle position have been confirmed, therapy may be administered through the needle, such as radiofrequency tissue treatment or other energy or non-energy mediated treatments. Exemplary energy treatment modalities include radiofrequency, microwave, high intensity focused ultrasound (HIFU), liquid infusion, plasma infusion, vapor, cryotherapy, and the like.

In another embodiment of the present invention, a needle is deployed in tissue by first positioning a probe having a deployable needle proximate a surface of the tissue. An image of the tissue is provided in real time, and a projected needle path is overlaid on the image. Prior to actually deploying the needle, the probe is repositioned to align the projected needle path on the real time image with anatomical feature. After the probe has been repositioned to optimize the position of the projected needle path within the anatomical feature, the needle may be deployed from the probe. After the needle has been actually deployed, the actual needle position may be fed back into the imaging system by marking a location on an image of the needle. Based on the actual needle position provided by the marked location, the projected safety boundary may be calculated by the system and overlaid on the image. Based on the projected safety boundary, the physician may visually confirm that sensitive anatomic structures are safe. Usually, the tissue image will also be overlaid with a projected treatment boundary based on the marked location. The physician may then also visually confirm that at least a portion of the anatomical feature to be treated is within the projected treatment boundary. The system may also be programmed so that the treatment device will be enabled only if the sensitive anatomic structures are outside of the safety boundary, typically by requiring the treating physician to acknowledge that the anatomical structures are safe.

Systems for deploying needles in tissue in accordance with the principles of the present invention comprise a probe and a system controller. The probe includes one or more deployable needles and an imaging transducer, where the needle(s) is (are) configured to be advanced into an image field produced by the imaging transducer. The system controller includes a screen for displaying the image produced by the transducer, where the system controller provides for an overlay on the screen with projected needle treatment information. The projected needle treatment information may comprise a projected needle path, where the physician can manipulate the probe to align the projected needle path with a target anatomy in the image field visible on the screen. The needle information may further comprise a projected treatment boundary and/or projected safety boundary. In such instances, the system may require the physician to confirm that the projected or actual needle position is safe and/or effective prior to enabling a therapy. Usually, the system will be able to update the projected needle information based on the actual needle position. In exemplary systems, the system controller further includes a generator for producing a therapy to be delivered through the needle, such as a radiofrequency, microwave, high intensity focused ultrasound (HIFU), vapor, liquid infusion, and cryotherapy. Systems may employ needle arrays comprising multiple needles.

Methods for treating fibroids and other anatomical features further comprise deploying at least one needle in the uterus proximate, usually within, the anatomical feature. The methods may deploy multiple needles in needle arrays. Radiofrequency energy is delivered into the feature through an exposed portion or portions of the needle, where no exposed needle portion is closer than 0.5 cm to the serosa, usually being no closer than 0.7 cm, and preferably being no closer than 1 cm. such methods can achieve effecting treatment of many or most fibroids or other features without damaging the serosa.

BRIEF DESCRIPTION OF THE DRAWINGS

FIGS. 2 through 4 illustrate an exemplary needle treatment probe which may be used in the methods and systems of the present invention for the treatment of uterine fibroids.

FIGS. 8A through 8G illustrate exemplary images which might be viewed by a treating physician when deploying the needle deployment probe of FIGS. 2 through 4 in treating a uterine fibroid generally as shown in FIGS. 6A and 6B.

DETAILED DESCRIPTION OF THE INVENTION

Figure 1:
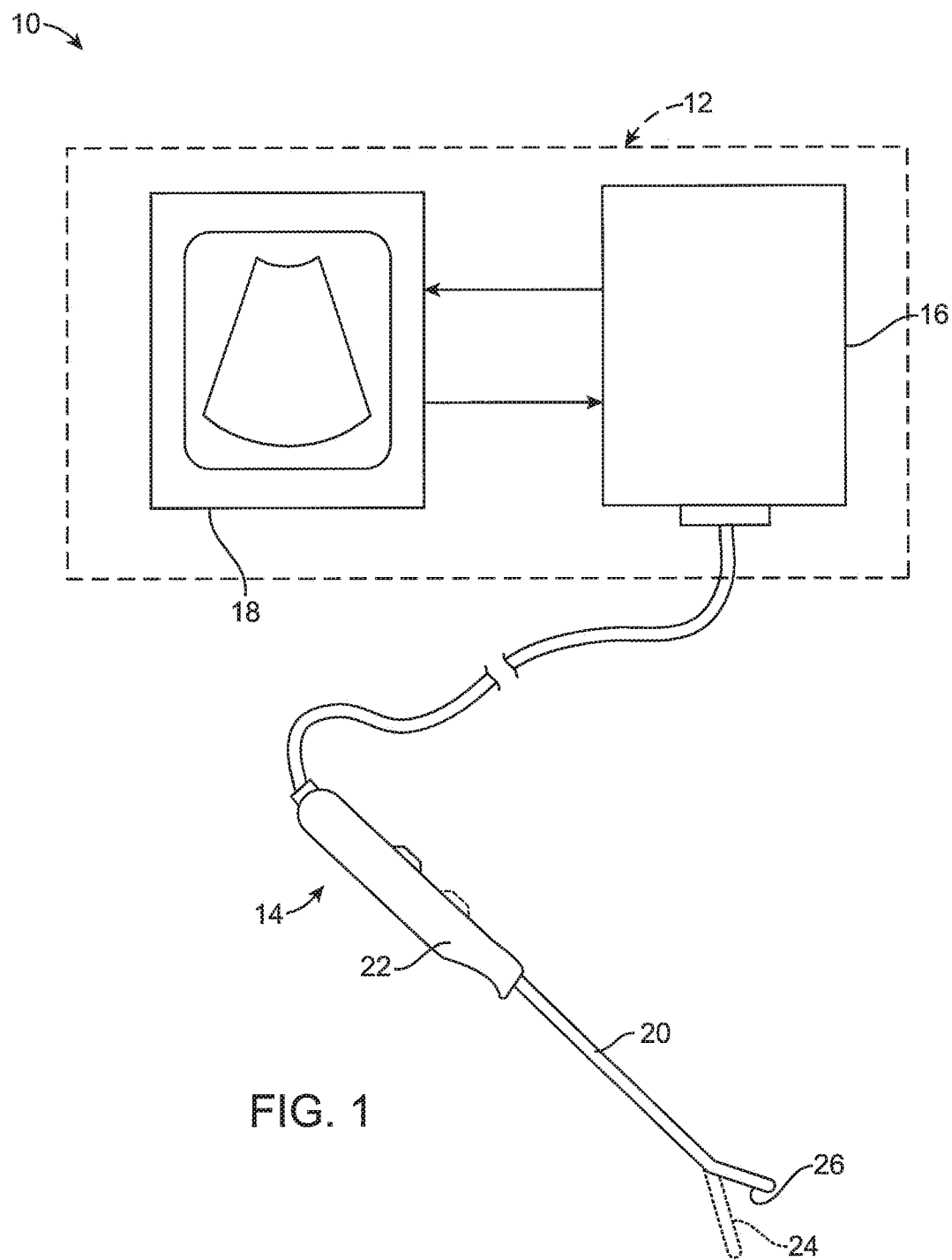
FIG. 1 is a schematic illustration of the system comprising a system controller and a needle treatment probe constructed in accordance with the principles of the present invention.

As illustrated in FIG. 1, a system 10 constructed in accordance with the principles of the present invention includes both a system controller 12 and treatment probe 14. The system controller 12 will include a processing and power unit 16 and a display screen 18. The controller 12 will further include means for the treating physician to input information, such as a keyboard, touch screen, control panel, or the like. The processing and power unit 16 will usually include a radiofrequency, microwave, vapor, treatment plasma, or other circuitry or mechanisms for delivering the treatment energy or other treatment agents to the treatment probe 14. Conveniently, the system controller 12 could comprise a conventional desktop or laptop computer to provide both the screen and logic and be connected to a separate radiofrequency, microwave, HIFU, liquid infusion, plasma infusion, vapor, cryotherapy or other source to provide the desired treatment.

Figure 4:
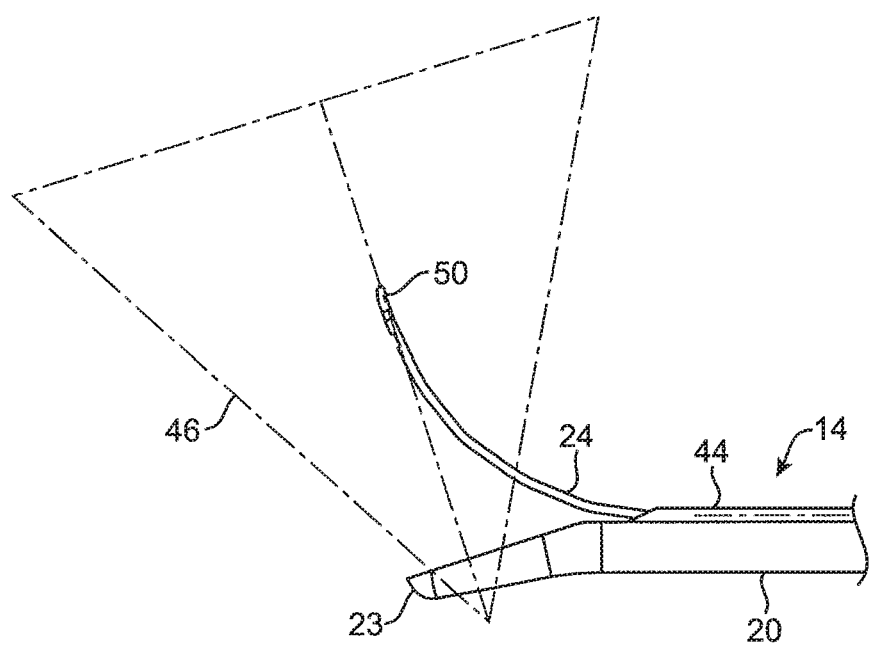

The treatment probe 14 typically includes a shaft 20 having a handle 22 at its proximal end. A needle 24 and imaging array 26 are provided at the distal end of the shaft 20, as described in more detail with reference to FIGS. 2 through 4. The treatment probe 14 shown in FIGS. 2 through 4 is described in more detail in copending provisional application No. 60/938,140, filed on May 15, 2007, the full disclosure of which has previously been incorporated herein by reference.

The probe 14 generally includes a rigid or other delivery shaft 20, an ultrasound imaging transducer 26, and an echogenic curved needle 24 with an artifact/feature 100 at a distal end 51 (FIG. 3) thereof. As shown, the artifact is a corner cut type retroreflector. The handle 22 is attached to a proximal end 21 of the shaft 20. A distal end 23 of the shaft 20 has a bent or deflectable distal tip, as best seen in FIG. 4. The ultrasound imaging transducer 26 comprises a linear ultrasound array disposed in a flat viewing window 36 (FIG. 3) which images in a field of view 46 (FIG. 4). Although only a single straight needle 24 is illustrated, the probe may carry multiple needles in arrays and/or the needles may be straight or have any other configuration.

The needle 24 is a solid tip electrically conductive needle intended for radiofrequency tissue ablation. As discussed elsewhere, it could also be intended for delivery of other forms of energy or be a hollow core needle intended for substance delivery or injection. The exemplary needle 24 generally comprises a two-piece construction including an elongate hollow body 48 (as best seen in FIG. 3) and a solid distal tip 50 at a distal end thereof. The distal tip 50 may be laser welded to the hollow tubular body 48. The solid tip 50 may also be attached via alternative means, for example adhesives or mechanical features or fits. The hollow tube 48 will generally have a length in a range from about 20 cm to about 45 cm. In some embodiments, the hollow tube will have an oval cross section having a thickness generally in a range from about 0.5 mm to about 2 mm and a wideness generally in a range from about 1 mm to about 3 mm. This flattened oval cross sectional shape, when present, is intended to inhibit lateral deflection during deployment or penetration of the needle 24. FIG. 3 also illustrates a representative laser cut hole 60 within the distal end of the tubular body 48 for the infusion of agents (e.g., electrolytes, drugs, etc.) so as to enhance the therapeutic effect of the needle 14 prior to or during ablation treatment. The infusion hole 60 may be aligned on one side of the tubular body 48 and generally has length in a range from about 0.5 mm to about 2 mm and a width in a range from about 0.5 mm to about 2 mm. It should be noted that hole 60 may comprise one or a plurality of holes, and each may be used for a different purpose.

The handle 24 further includes a longitudinally movable slider 72 for enabling the advancement and retraction of the needle 14 to and from within a needle guide 44. The ultrasound imaging transducer 26 may optionally be present on an imaging insert replaceably disposed within the axial passage of the shaft 20. A sealing element 30 may be provided between the ultrasound imaging transducer 26 and the shaft handle 24 to ensure sufficient sealing around the insert at a proximal end. It will be appreciated that the above depictions are for illustrative purposes only and do not necessarily reflect the actual shape, size, or dimensions of the system 10. Furthermore, the ultrasound array may be parallel to an axis of the shaft 20 or may be slightly inclined as illustrated in FIG. 4. This applies to all depictions hereinafter. The array is typically a linear array with from 16 to 128 elements, usually having 64 elements. The length (azimuth) of array 12 usually ranges from about 5 mm to about 20 mm, normally being about 14 mm. The array may have a depth (elevation) ranging from about 1 mm to about 8 mm, normally being about 2 mm. In an embodiment, the ultrasound array transmits ultrasound waves at a center frequency ranging from about 2 MHz to about 15 MHz, typically from about 5 MHz to about 12 MHz, normally about 6.5 MHz.

Figure 5:
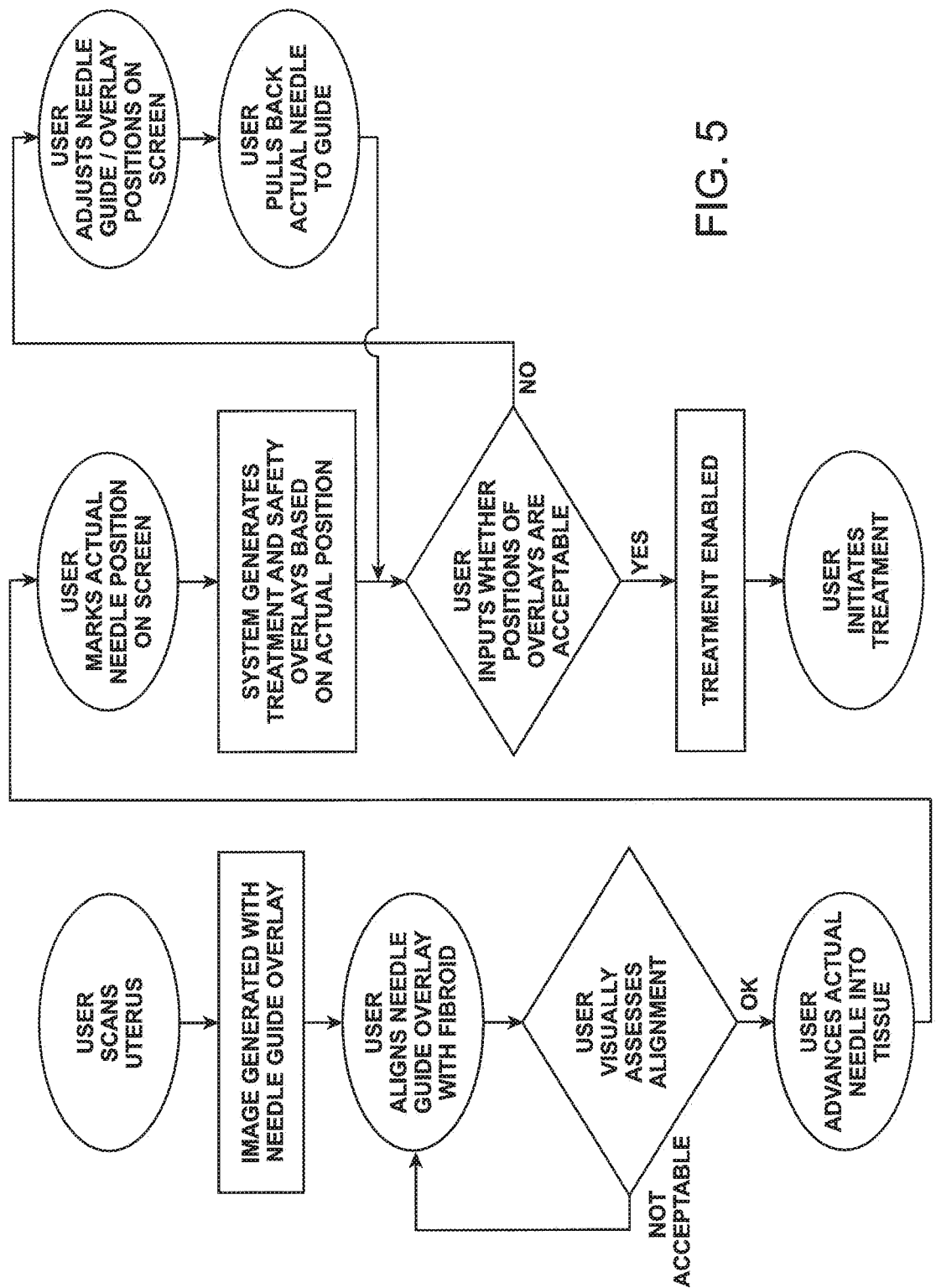
FIG. 5 is a flowchart illustrating an exemplary treatment protocol in accordance with the principles of the present invention.
Figure 6A:
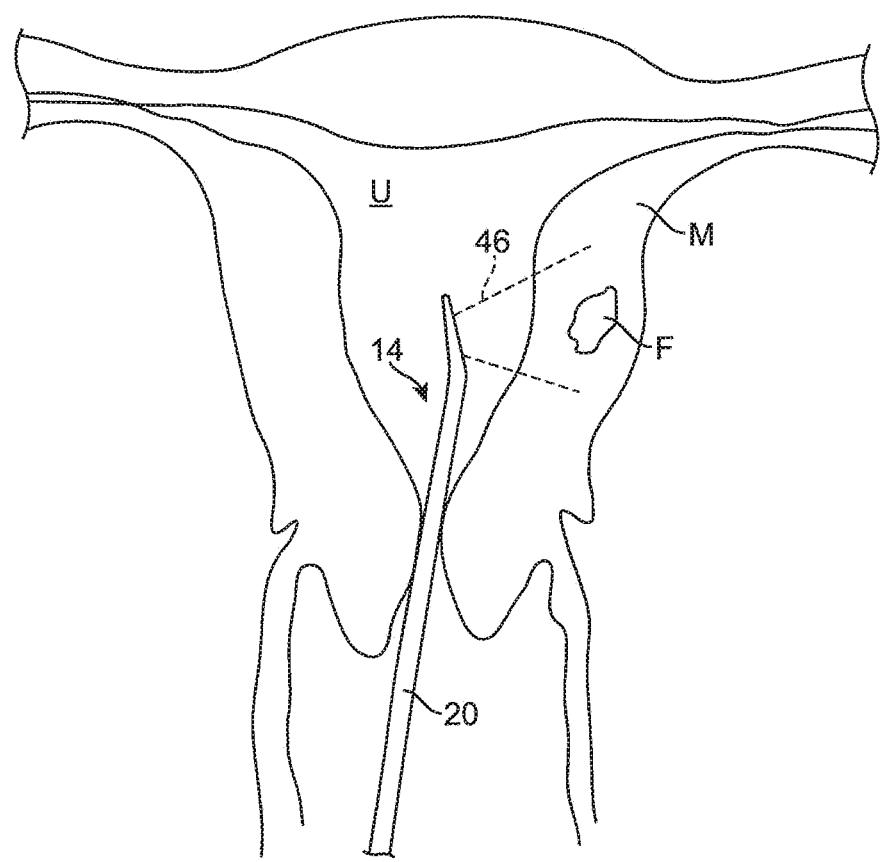
FIGS. 6A and 6B illustrate use of the needle treatment probe of FIGS. 2 through 4 in the treatment of a uterine fibroid in accordance with the principles of the present invention.

Referring now to FIG. 5, an exemplary protocol for performing the needle positioning methods of the present invention for treating uterine fibroids will be described. After the probe 14 is positioned in the uterus, the treating physician scans the myometrium M in order to locate fibroids F, as shown in FIG. 6A. Shaft 20 is manipulated so that the field of view 46 of the transducer array 26 provides a visual image, such as that shown in FIG. 8A, on the screen 18 of the system 12. Once a fibroid F is located, the physician can scan the image for other anatomical features such as the treatment-sensitive serosa S, as also shown in FIG. 8A. It should be appreciated that the image being produced is "real time," and that the image will change as the physician moves the shaft 20 within the uterus U so that the field of view 46 scans over different portions of the myometrium.

Figure 8B:
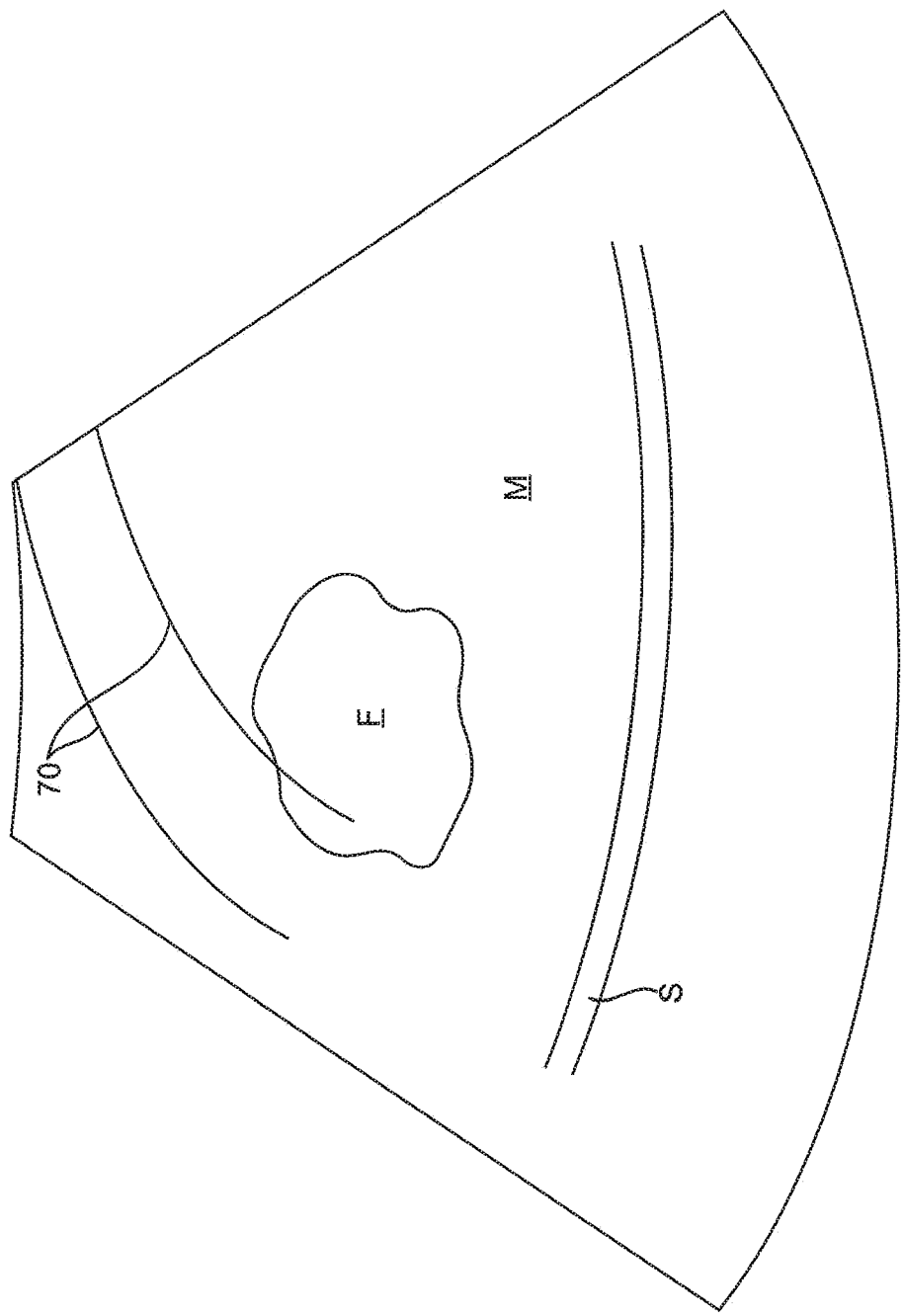

The next step in the protocol of FIG. 5 relies on aligning a needle guide overlay with the fibroid. The needle guide may be a simple pair of parallel lines 70, as shown in FIG. 8B. The parallel lines 70 will typically represent the limits of the most likely lateral needle advancement path. Thus, by aligning the lines 70 generally across the target fibroid F, as shown in FIG. 8C, the likelihood that the needle will be directed into the middle of the fibroid is increased.

Figure 6B:
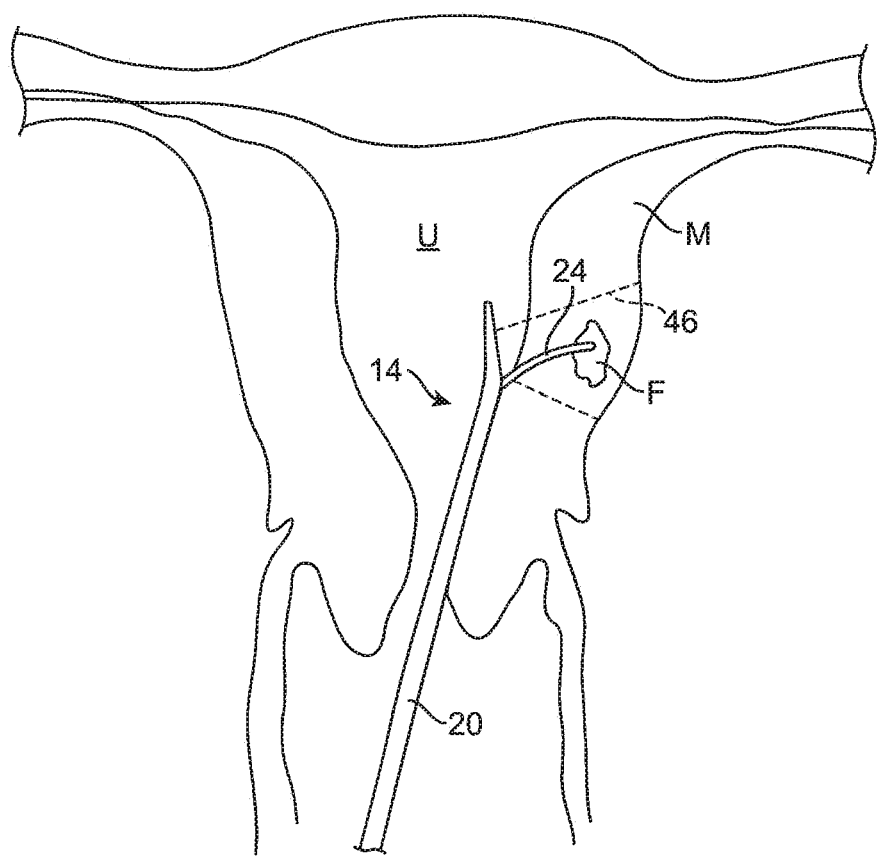
Figure 8C:
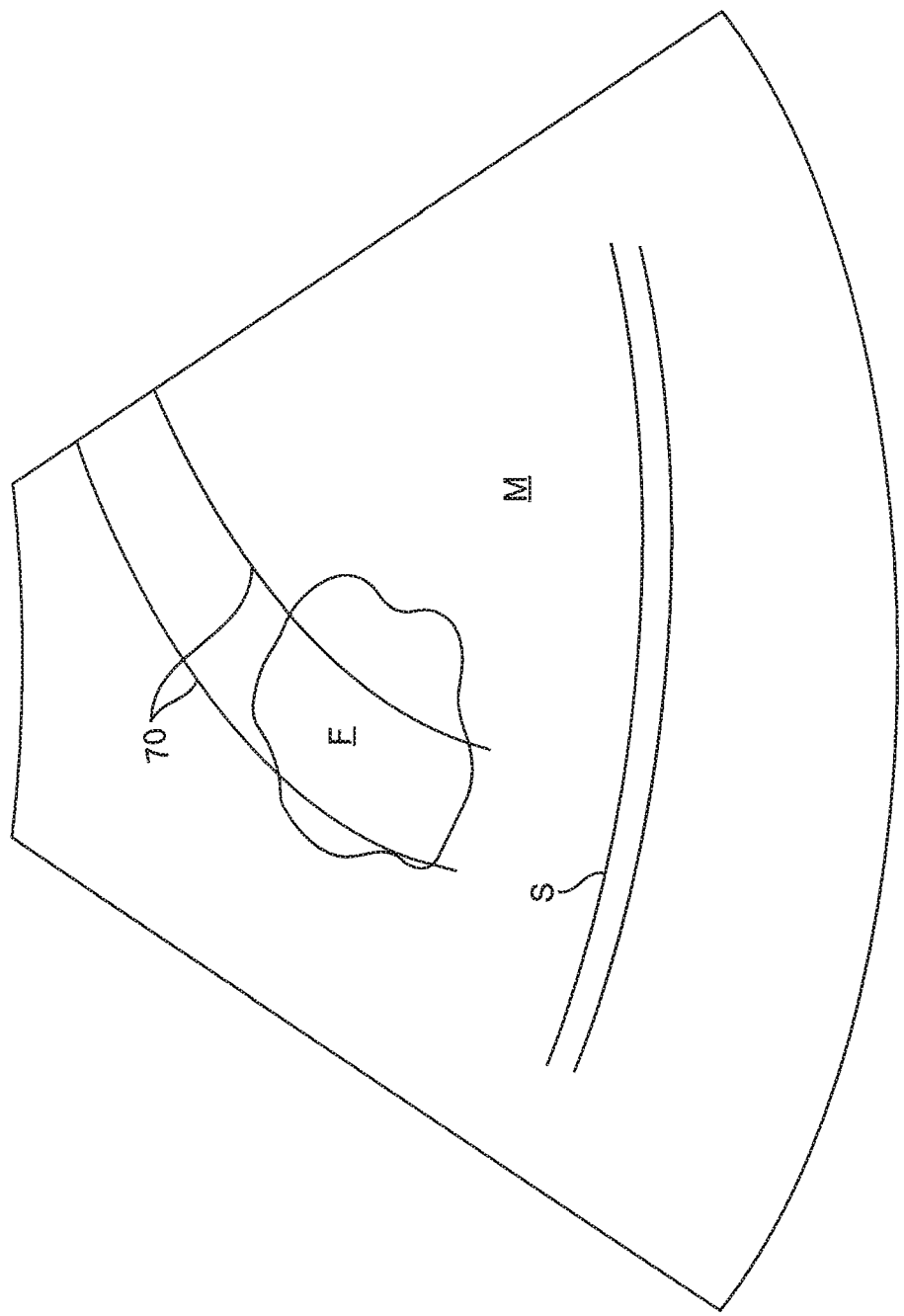
Figure 8D:
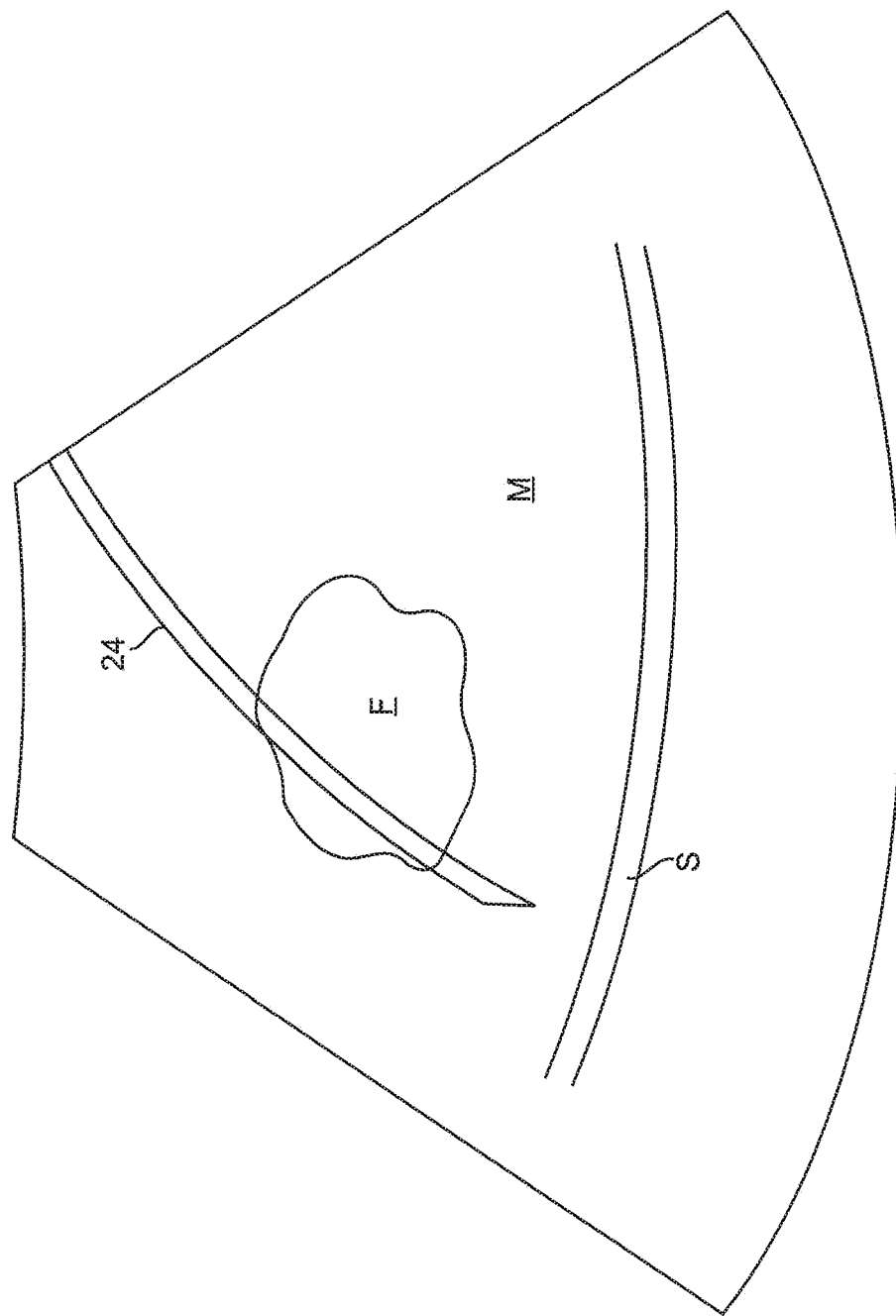
Figure 8E:
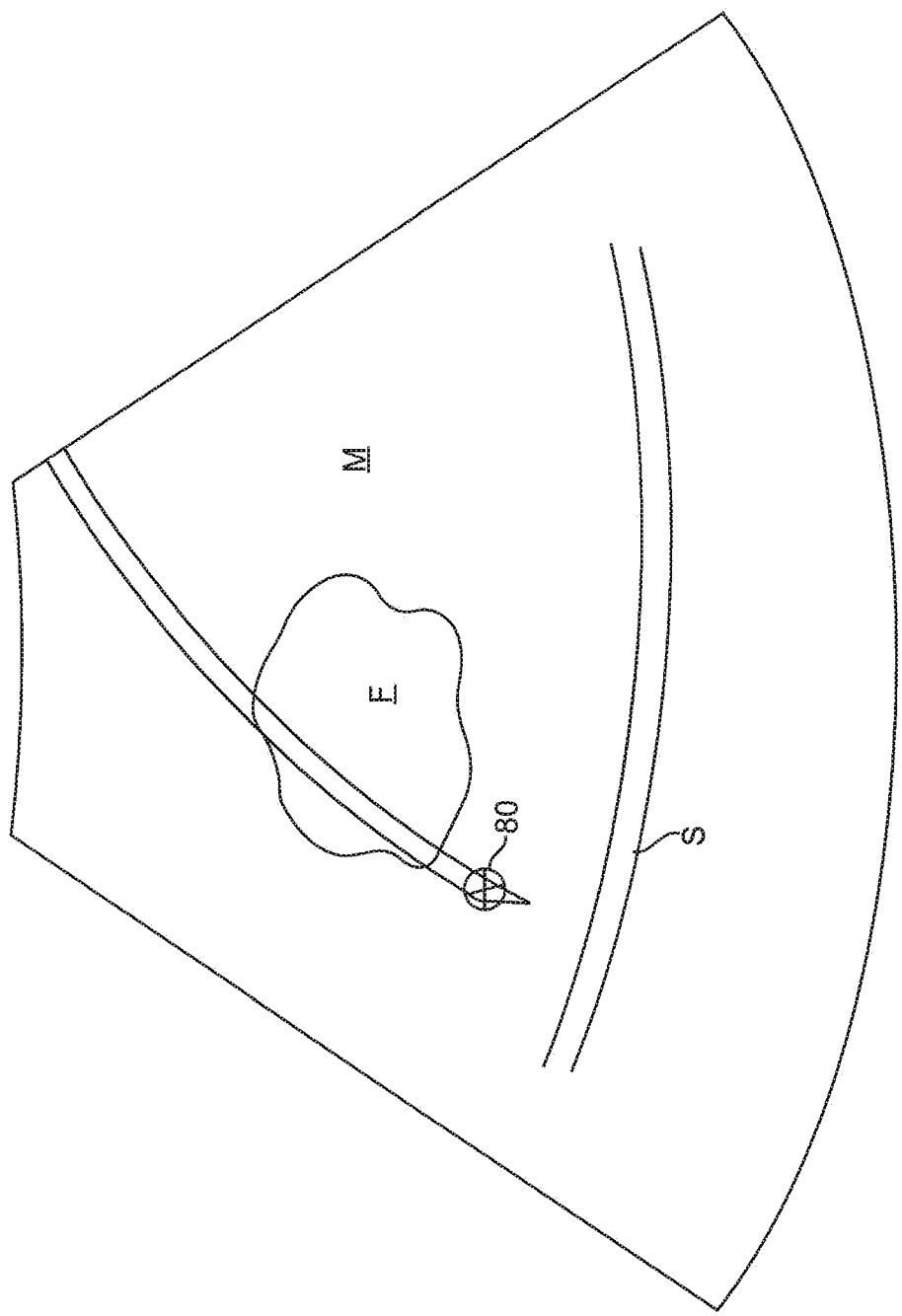

The treating physician continues to visually assess the position of the needle guidelines 70 relative to the fibroid F until they are acceptably aligned, as shown in FIG. 8C. The physician then advances the actual needle into the tissue as shown in FIG. 6B, where the image of the actual needle is shown in FIG. 8D. After the image of the actual position of the needle appears, the physician marks a preselected position on the needle, either by moving a curser on the image and clicking, touching the screen, or the like. Such "marking" of the actual position allows the system to calculate or recalculate a projected safety boundary and a projected therapy region. For example, the system may be marked near the tip of the needle, as shown at location 80 on FIG. 8E.

Figure 7:
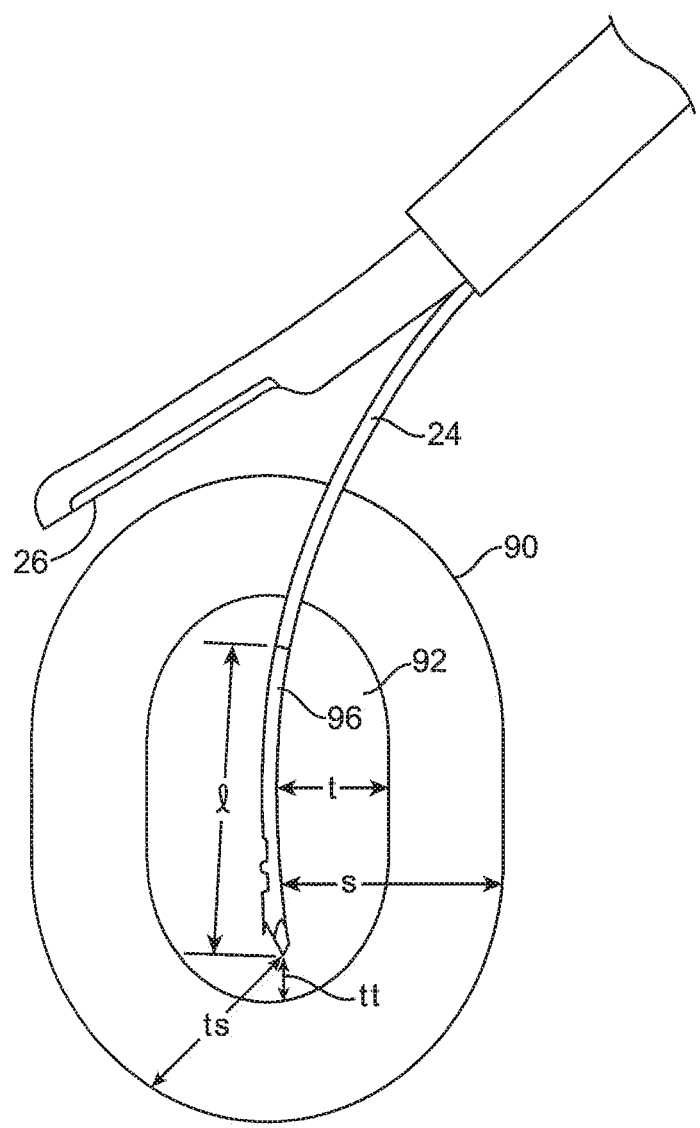
FIG. 7 illustrates exemplary dimensions for a treatment region and a safety boundary for the needle deployment probe of FIGS. 2 through 4.

Referring now to FIG. 7, an exemplary safety boundary 90 and treatment region 92 for a single needle fibroid ablation system will be described. A treatment needle 24 has an uninsulated treatment portion 96 having a length 1 in the range from 1 cm to 3 cm, typically being 2 cm. The safety boundary will be an oval line which is generally a distance s from the exposed exterior of the treating electrode portion 96. The distance s is usually in the range from 1 cm to 3 cm, typically being about 1.5 cm. A distance t between the exposed needle portion 96 and the treatment region boundary 92 will typically be about half that of the safety distance s, typically being in the range from 0.5 cm to 1.5 cm, usually being about 0.75 cm. Generally, the distance tt from the distal tip of the needle 24 and the safety boundary and the treatment region perimeter will be somewhat less because of the reduced energy density at the tip. Thus, the distance tt between the tip and the treatment region perimeter may be from 0.1 cm to 0.5 cm, usually being about 0.25 cm while the distance is between the tip and the safety boundary will be in the range from 0.5 cm to 1.5 cm, typically being about 1 cm.

Based on these desired clearance distances, the system projects treatment and safety overlays on the actual image of the needle 24, as shown in FIG. 8F. The physician can then visually assess whether sensitive tissue structures, such as the serosa S remain outside of the projected safety boundary 90. As shown in FIG. 8F, the serosa S is inside of the safety boundary 90, so it will be necessary to reposition or redeploy the needle 24 to move the serosa S beyond the safety boundary. It is noted that the position of the treatment perimeter 92 about the fibroid F is probably sufficient for treatment, but the needle needs to be deployed based on safety concerns.

Figure 8G:
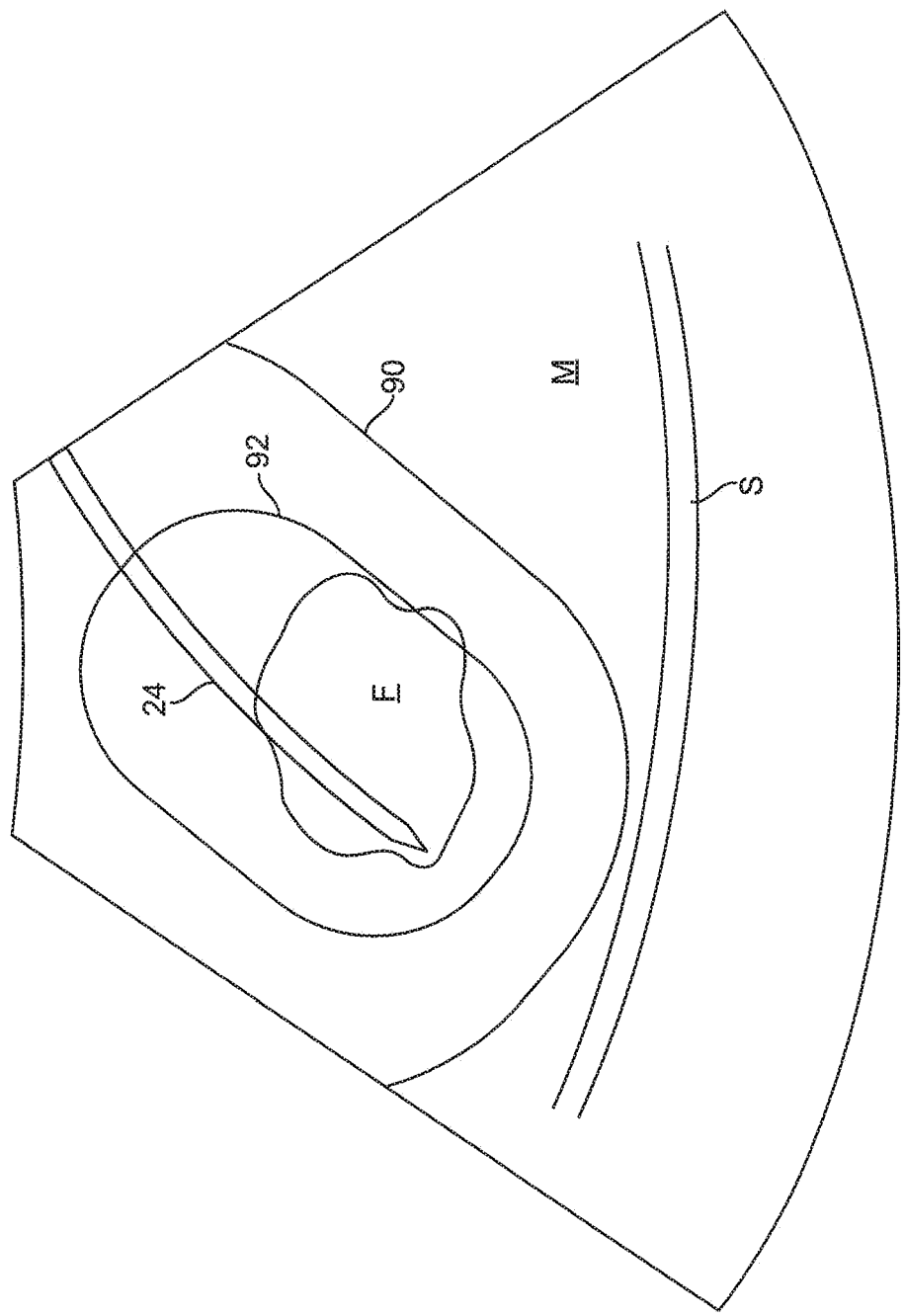

Once the needle has been repositioned or redeployed so that the treatment region 92 sufficiently covers the fibroid F while the safety boundary does not encroach upon the serosa S as shown in FIG. 8G, the physician will enable the system for treatment. Usually, the system will require the physician to acknowledge that the needle has been properly positioned before allowing the system to power the needle. Once that is done, the physician can initiate treatment, as described generally in the prior applications which have been incorporated herein by reference.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for treating uterine anatomy, the system comprising:
   an ultrasound imaging device configured to produce a real-time image of the uterine anatomy including a uterine fibroid to be treated;

a radiofrequency ablation device comprising a needle array comprising multiple needles, wherein the needle array is deployable into the uterine fibroid; and a system controller comprising:
- a screen for displaying the real-time image of the uterine anatomy produced by the ultrasound imaging device;
- a radiofrequency generator; and
- a processing unit programmed to:
  - overlay a projected treatment boundary or projected treatment volume based on a position of the needle array onto the real-time ultrasound image of the uterine anatomy;
  - recalculate the projected treatment boundary or projected treatment volume based on an actual position of the needle array deployed into the uterine fibroid; and
  - deliver radiofrequency energy from the radiofrequency generator through the needle array after recalculating the projected treatment boundary or projected treatment volume and with at least a portion of the uterine fibroid positioned within the recalculated projected treatment boundary or projected treatment volume on the real-time ultrasound image.

2. The system of claim 1, wherein the processing unit is programmed to overlay the projected treatment boundary or projected treatment volume based on a position of the needle array onto the real-time ultrasound image of the uterine anatomy prior to deploying the needle array into the uterine fibroid.

3. The system of claim 1, wherein the processing unit is programmed to overlay onto the real-time ultrasound image a projected needle path of the radiofrequency ablation device as the radiofrequency ablation device is being manipulated relative to the uterine fibroid to be treated.

4. The system of claim 1, wherein the processing unit is programmed to prevent the delivering of radiofrequency energy until confirmation indicative of treatment being safe or effective.

5. A system for treating uterine anatomy, the system comprising:
- an ultrasound imaging device configured to produce a real-time image of the uterine anatomy including an anatomical feature to be treated;
- a tissue treatment device comprising one or more needles; and
- a system controller comprising:
  - a screen for displaying the real-time image of the uterine anatomy produced by the ultrasound imaging device; and
  - a processing unit programmed to:
    - overlay onto the real-time ultrasound image of the uterine anatomy projected needle treatment information of the tissue treatment device when the tissue treatment device is positioned proximate to the uterine anatomy, wherein the projected needle treatment information is predicted based on a deployed position of the one or more needles, and wherein the projected needle treatment information includes a projected treatment boundary surrounding a portion of the one or more needles when in a deployed position;
    - align the projected needle treatment information on the real-time ultrasound image with the anatomical feature to be treated such that at least a portion of the anatomical feature to be treated is within the projected treatment boundary;
    - recalculate the projected treatment boundary based on an actual position of the one or more needles deployed into the anatomical feature to be treated; and
    - deliver energy through the one or more needles to treat the anatomical feature after aligning the projected needle treatment information on the real-time ultrasound image and with the one or more needles deployed into the anatomical feature to be treated and after recalculating the projected treatment boundary.

6. The system of claim 5, wherein the processing unit is programmed to overlay the projected treatment boundary onto the real-time ultrasound image after the one or more needles of the tissue treatment device are deployed into the anatomical feature.

7. The system of claim 5, wherein the processing unit is programmed to overlay the projected treatment boundary onto the real-time ultrasound image before the one or more needles of the tissue treatment device are deployed into the anatomical feature to be treated.

8. The system of claim 5, wherein the anatomical feature to be treated comprises a uterine fibroid.

9. The system of claim 5, wherein the processing unit is programmed to overlay onto the real-time ultrasound image a projected needle deployment path.

10. The system of claim 5, wherein the processing unit is programmed to overlay onto the real-time ultrasound image a safety boundary based on the deployed position of the one or more needles of the tissue treatment device.

11. A system for treating uterine anatomy, the system comprising:
- an ultrasound imaging device configured to produce a real-time image of the uterine anatomy including an anatomical feature to be treated;
- a tissue treatment device comprising one or more needles; and
- a system controller comprising:
  - a screen for displaying the real-time image of the uterine anatomy produced by the ultrasound imaging device; and
  - a processing unit programmed to:
    - overlay onto the real-time ultrasound image a projected needle path of the tissue treatment device when positioned proximate to the uterine anatomy;
    - overlay onto the real-time ultrasound image a projected treatment boundary or projected treatment volume based on a deployed position of the one or more needles of the tissue treatment device, wherein at least a portion of the anatomical feature to be treated is within the projected treatment boundary or projected treatment volume;
    - recalculate the projected treatment boundary or projected treatment volume based on an actual position of the one or more needles deployed into the anatomical feature to be treated; and
    - deliver energy through the one or more needles to treat the anatomical feature after the projected treatment boundary or projected treatment volume is overlaid onto the real-time ultrasound image and with the one or more needles deployed into the anatomical feature to be treated and after the projected treatment boundary or projected treatment volume is recalculated.

12. The system of claim 11, wherein the tissue treatment device comprises an array of multiple needles.

13. The system of claim 11, wherein the processing unit is programmed to overlay the projected treatment boundary or projected treatment volume onto the real-time ultrasound image after the one or more needles are deployed into the anatomical feature to be treated.

14. The system of claim 11, the processing unit is programmed to overlay the projected treatment boundary or projected treatment volume onto the real-time ultrasound image before the one or more needles are deployed into the anatomical feature to be treated.

15. The system of claim 11, wherein the processing unit is programmed to overlay the projected needle path and the projected treatment boundary or projected treatment volume simultaneously onto the real-time ultrasound image.

16. The system of claim 15, wherein the processing unit is programmed to overlay the projected treatment boundary or projected treatment volume onto the real-time ultrasound image while the projected needle path is being manipulated relative to the anatomical feature to be treated.

17. The system of claim 11, wherein the projected treatment boundary or projected treatment volume surrounds a portion of the one or more needles when in the deployed position.

18. The system of claim 17, wherein the projected treatment boundary or projected treatment volume has an oval shape.

19. The system of claim 11, wherein the processing unit is programmed to overlay the projected needle path and the projected treatment boundary or projected treatment volume onto an image of the one or more needles of the tissue treatment device.

20. The system of claim 11, wherein the anatomical feature to be treated comprises a uterine fibroid.

21. The system of claim 11, wherein the processing unit is programmed to overlay onto the real-time ultrasound image a safety boundary based on the deployed position of the one or more needles of the tissue treatment device.

* * * * *